(12) United States Patent
Barbarin (10) Patent No.: US 10,287,538 B2
(45) Date of Patent: May 14, 2019

(54) DEVICE FOR PRODUCING A PHOTOSYNTHETIC CULTURE BY MEANS OF A PHOTO-BIOREACTOR AND AT LEAST ONE LIGHT DISTRIBUTOR

(71) Applicant: SUNOLEO, Pertuis (FR)

(72) Inventor: Frederic Barbarin, Obterre (FR)

(73) Assignee: SUNOLEO, Pertuis (FR)

( * ) Notice: Subject to any disclaimer, the term of this patent is extended or adjusted under 35 U.S.C. 154(b) by 47 days.

(21) Appl. No.: 15/532,268

(22) PCT Filed: Dec. 2, 2015

(86) PCT No.: PCT/FR2015/053294
§ 371 (c)(1),
(2) Date: Jun. 1, 2017

(87) PCT Pub. No.: WO2016/087779
PCT Pub. Date: Jun. 9, 2016

(65) Prior Publication Data
US 2017/0342361 A1 Nov. 30, 2017

(30) Foreign Application Priority Data

Dec. 2, 2014 (FR) ...................... 14 61778

(51) Int. Cl.
*C12M 1/00* (2006.01)
*C12M 1/02* (2006.01)
*C12M 1/09* (2006.01)
(52) U.S. Cl.
CPC ............ *C12M 21/02* (2013.01); *C12M 23/26* (2013.01); *C12M 23/38* (2013.01); *C12M 23/56* (2013.01); *C12M 27/00* (2013.01); *C12M 31/08* (2013.01)

(58) Field of Classification Search
CPC ...... C12M 21/02; C12M 31/08; C12M 27/00; C12M 23/26; C12M 23/38; C12M 23/56
See application file for complete search history.

(56) References Cited

U.S. PATENT DOCUMENTS 4,900,678 A 2/1990 Mori
2014/0073035 A1 3/2014 Friederich et al.

FOREIGN PATENT DOCUMENTS

EP 0 112 556 A1 7/1984
JP 2000228973 A 8/2000
(Continued)

OTHER PUBLICATIONS

Database WPI Week 200058 Thomson Scientific, London, GB AN 2000-605213 XP002745063.
(Continued)

*Primary Examiner* — Gautam Prakash
(74) *Attorney, Agent, or Firm* — Young & Thompson (57) ABSTRACT

Disclosed is a photosynthetic culture production device including at least one photo-bioreactor chamber having a supply/discharge unit, and including: an aqueous liquid containing a photosynthetic culture; at least one unit for supplying and discharging fluids from the chamber interacting with a management system; at least one light distributor including at least one first wall arranged so as to receive the light at a proximal end, at least one second wall arranged so as to emit at least part of the received light, and a sealed cavity defined by the at least one first wall and the at least one second wall, part of the emitting wall being immersed in the aqueous liquid containing the photosynthetic culture; at least one fluid partially filling the sealed cavity; and a cover, limiting evaporation. The cover has at least one opening, keeping the at least one light distributor stationary in the chamber.

19 Claims, 4 Drawing Sheets

(56) References Cited

FOREIGN PATENT DOCUMENTS

| WO | 2009/116853 A1 | 9/2009 |
| WO | 2012/152637 A1 | 11/2012 |
| WO | 2013/011448 A1 | 1/2013 |
| WO | 2013/063075 A2 | 5/2013 |

OTHER PUBLICATIONS

International Search Report, dated Feb. 12, 2016, from corresponding PCT application.

DEVICE FOR PRODUCING A PHOTOSYNTHETIC CULTURE BY MEANS OF A PHOTO-BIOREACTOR AND AT LEAST ONE LIGHT DISTRIBUTOR

TECHNICAL FIELD OF THE INVENTION

The invention relates to the field of photosynthetic culture production devices, and in particular by means of a photo-bioreactor.

PRIOR ART

The culture of micro-algae is at the core of recycling methods. Indeed, micro-algae are an alternative source in particular for the production of biofuel, biomass, oils, proteins, esters or ethanol. Furthermore, such cultures can be used for the recycling and the purification of waste water, treating fertiliser discharges, $CO_2$, $NOx$, $SOx$, from certain factories.

The development of photosynthetic cultures of micro-algae requires however setting up specific production systems, to be adapted according to the target application, the industrial operating conditions, the strain to be cultivated, the geographical, climatic or sunshine conditions.

Furthermore, a well-known difficulty in this field relates to the penetration of the light into the photo-bioreactor. Indeed, on a given surface of land, a simple horizontal body of water, such as "raceways" (photo-bioreactor with a large open basin, of shallow depth), only partially uses the solar potential since, from a few centimeters in depth, the opacity of the water according to its concentration in micro-algae, limits the penetration of the light in depth. The surplus of direct light that cannot pass through the opacity of the culture mediums (or algal water) is then partially absorbed by the latter in the form of heat, instead of being used for the growth of the micro-algae, leading to a problem of water evaporation.

Furthermore, the "raceways" can generate problems linked to outside contaminations (bacterial, predators, concurrent algae introduced, etc.) which harm production. Another disadvantage of "raceways" concerns the high rate of water evaporation.

To overcome these problems, photo-bioreactors with fine watertight layers have been developed. However, a cooling system is indispensable in order to prevent an alteration of the micro-algae, making the management of the culture more complicated and decreasing its output. Indeed, these photo-bioreactors require complex management equipment proportionally to the volume of water used, which implies that their industrialisation is impossible for mass production.

Another embodiment was developed in which the photo-bioreactors use light diffusers within in order to increase the useful volume of water for the production of micro-algae.

Such devices are described in international application WO2013/063075, wherein LEDs were arranged inside the photo-bioreactor in order to increase the output of the photosynthetic culture.

Furthermore, certain bioreactors of prior art have a relatively complex construction and sometimes use complex optics to illuminate the algal water.

This type of device requires a supply of energy which increases the cost price of the culture of micro-algae. Consequently, sunlight is often preferred.

Document WO 2012/152637 discloses a photobioreactor, wherein a light diffuser element placed in the culture chamber is optically coupled to an artificial light source, for example one or several LEDs. Furthermore this device is not suited to a culture basin of large size, in that the light diffusers which are not filled with fluid cannot resist an excessive hydrostatic pressure of the water.

International application WO 2009/116853 has an alternative for light diffusers, here sunlight by the adding in the tank of a transparent rigid device comprising at least one surface for receiving light arranged so as to receive sunlight and at least one surface for emitting, immersed in the algal water, arranged so as to emit at least one part of the received light in the algal water.

This type of photo-bioreactor in addition to using materials with thick and expensive walls, requires substantial exposure to solar radiation, which increase the evaporation of the algal water and renders the management of the photosynthetic culture more complicated.

Furthermore, such light diffusers occupy a very large amount of space regardless of the type of tanks used. This makes the maintenance, replacing and use of them difficult in photo-bioreactors of industrial size.

International application WO 2013/011448 describes a photo-bioreactor wherein light distributors comprised of sleeves made from a flexible and transparent material that is traction and pressure resistant, are suspended vertically from a support and immersed in the algal solution. The support more preferably closes the basin. This support therefore must have the mechanical resistance required to support the weight of all of the sleeves filled with water, which limits the size of the basins.

DISCLOSURE OF THE INVENTION

The invention aims to overcome the disadvantages of prior art and in particular to propose a device for producing a photosynthetic culture comprising at least one photo-bioreactor forming a chamber having a supply/discharge means and comprising:
  an aqueous liquid comprising a photosynthetic culture,
  at least one means for supplying and discharging fluids from said chamber interacting with a management system,
  at least one light distributor comprising:
    at least one first wall arranged so as to receive the light at a proximal end,
    at least one second wall arranged so as to emit at least one part of the received light,
    a sealed cavity defined by said at least one first and one second walls,
    at least one part of the emitting wall is immersed in the aqueous liquid comprising the photosynthetic culture,
    at least one fluid, at least partially filling said sealed cavity,
  a means for covering said photo-bioreactor capable of limiting the evaporation of said aqueous liquid,
characterised in that said covering means has at least one opening, capable of keeping said at least one light distributor in a stationary position in said chamber of the photo-bioreactor.

The term "aqueous liquid comprising a photosynthetic culture" means preferably any cultures of micro-algae; the micro-algae are chosen according to the target application (for example the production of proteins, oil, ethanol, biomass) and the culture conditions, in particular geographical, climatic and temperature. Furthermore, the term "aqueous liquid comprising a photosynthetic culture" can be replaced with "algal water" without having an influence on the scope of the protection granted by this application.

The term "fluid" means any liquid or gas suitable for the operation of the photo-bioreactor or the development of the photosynthetic culture.

The term "light distributor" means any body that has at least two walls, with the first receiving light radiation, preferably from the sun, the second emitting at least one part of the light radiation. Preferably, said body is a cylinder or a variation of a cylinder extending for its height, along an axis X orthogonal to the support plane whereon said chamber of said photo-bioreactor rests. Furthermore, the height of said at least one light distributor is close to the height of said chamber. That is to say that the height of said at least one light distributor is between 100% and 85% of the height of said chamber.

The term "proximal end" means the end that is the farthest away from the support plane for a normal use of said at least one light distributor, i.e. when the latter is immersed in the photo-bioreactor of axis X.

The term "distal end" means the end that is the closest to the support plane for a normal use of said at least one light distributor.

The term "covering means" means any means that makes it possible to close the upper surface of said photo-bioreactor in order to form a sealed chamber, preferable hermetically, for example, a cover, a tarp, or any other technically equivalent means. Furthermore the covering means can be transparent or opaque, coloured, and it can be made from a cut and welded strip of polymer, or of a single piece.

Advantageously, a cooperation of form between at least one edge of said opening of said covering means and a surface relief of said at least one light distributor is carried out, so as to maintain said at least one light distributor in a stationary position in said chamber of the photo-bioreactor.

Preferentially, said light-receiving wall of said at least one light distributor is arranged outside of the volume defined by said chamber of the photo-bioreactor.

In other terms, at least one part of said at least one light distributor is not covered by the covering means and exceeds said covering means, in such a way that the plane formed by said covering means separates said at least one first and one second walls from said at least one light distributor.

Advantageously, the number (nbdistributor), the immersed height (Hdistributor) of said at least one light distributor and the spacing (d) between the different light distributors are determined using the following formulas:

In a chamber of circular or rectangular transversal section of surface Schamber (in m2), $$nb_{distributeur} = \frac{4 \cdot \xi \cdot S_{enceinte}}{\pi \cdot D^2} \quad (1)$$

distributeur=distributor
enceinte=chamber
ξ: the volume fraction occupied by the light distributors, compared to the total volume of water in the chamber.
The fraction ξ is preferably between 0.6 to 0.8.
D: the diameter of the light distributor (in m).
This preceding equation does not take edge effects into account.

$$H_{distributeur} = \frac{D}{4 \cdot q_2}(\eta \cdot q_{solaire} - q_2) \quad (2)$$

distributeur=distributor
enceinte=chamber

Hdistributor: Height of the second wall of the light distributor (immersed portion) (in mm)
qsolar: incident flux of a sunny day (in μmoles of photons/m2·s−1),
q2: luminous flux desired at the light emitting wall of the light distributor for good production of a given strain of micro-algae (in μmol/m2·s−1).
η: the transmission output between the first light receiving wall and the second emitting wall of the light distributor.

The height Hdistributor can be between 1 m and 12 m, preferably between 4 m and 8 m, while the diameter of the light distributor can be between 1 m and 3 m.

$$d = \sqrt{\frac{\pi \cdot D^2}{4 \cdot \xi \cdot \cos 30}} \quad (3)$$

d: distance in meters between the longitudinal axes X of 2 light distributors.

Preferably, said at least one light distributor is provided with means for supplying and extracting fluids. Said means for supplying and extracting fluids are able to be independent, partially or entirely confounded with each other.

Preferably said at least one fluid, at least partially filling said sealed cavity is comprised of water and of air. As such, the immersion of said at least one light distributor in the algal water is controlled by the water/air ratio present in said cavity of said at least one light distributor.

Furthermore, said fluid, at least partially filling said sealed cavity is able to pressurise the interior volume of said at least one light distributor in such a way as to seal the cooperation of form between the edge of said opening and said surface relief of said at least one light distributor.

Moreover, said light distributors float and make it possible to support the covering means above the plane of algal water, advantageously at a distance between 10 cm and 50 cm. As such, in such an embodiment of the invention, the light distributors act as floaters maintaining the covering means above the plane of algal water. The maintaining of the covering means above the plane of algal water allows for the circulation of gases between the surface of the algal water and the covering means. Such an embodiment of the device of the invention makes it possible to overcome the use of a rigid support above the plane of algal water and consequently the problem of the bearing capacity. It is as such possible to use, without limitation, a culture basin of large size. As such the covering means can be a non-rigid structure such as a simple tarp.

Advantageously, said at least one light distributor is provided with a means of anchoring arranged at a distal end.

The term "means of anchoring" means any attached or unattached mass at the bottom of the photo-bioreactor, any means of connection between said at least one light distributor and the bottom of the photo-bioreactor such as a cord, a chain, or any other means known to those skilled in the art, able to immobilise in a desired position said at least one light distributor.

According to another characteristic, said walls of said at least one light distributor are formed by at least one flexible membrane with more preferably, a high degree of transparency and a resistance to elasticity. Such a flexible membrane can be made of polymer, for example of polyethylene, polypropylene or polyamide, or PVC, or a multilayer of polymers having properties that are complementary.

As such, according to this characteristic, said at least one light distributor is inflatable/deflatable. That is to say that in order to obtain its form of use, said at least one light distributor must have said sealed cavity filled with fluid, in particular with water and air, and have a pressure that is higher than atmospheric pressure, preferably about 50 hectopascals.

Moreover, the polymer of the membrane can have a certain degree of a seal to oxygen, over its entire surface or locally, in order to limit the porosity of the walls of the light diffuser. According to the improvement of the management of the air in the proximal portion of the light diffuser, several channels can be retained. Either seeking to limit as much as possible the gaseous exchanges with the outside environment in order to decrease the supply of air in order to maintain the light diffuser at its level of immersion. In this solution, the porosity to oxygen could for example be less than 0.1 cm3/m2·day−1. Or on the contrary, to facilitate the discharge of the oxygen from the algal water to the water of the light diffuser.

Furthermore, when said sealed cavity of said at least one light distributor does not contain fluid, in particular when it is stored or not yet installed in said photo-bioreactor, said at least one light distributor can be folded, rolled in order to limit the space it occupies.

Advantageously, said membrane made of polymer received or comprises when it is produced at least one internal and/or external surface treatment from among the following: anti-drip, anti-dust, UV and/or infrared filter, UV stabilisers, diffusing effect, semi reflective, hydrophobic, anti-dust, anti-algae (for example: titanium oxides).

For example, a treatment with titanium oxides makes it possible to prevent on the first wall, which receives the sunlight, the formation of drops of condensation that can disturb the passage of the light in said at least one light distributor and on the second wall to prevent the phenomenon of "fouling", i.e. the depositing of algae on the walls.

A treatment on the interior surface with a long infrared filter makes it possible to retain the long infrared in the light distributor in order to heat the interior via the greenhouse effect.

An anti-UV treatment makes it possible to prevent the destruction of the photosynthetic culture by the UVs.

A semi-reflective treatment allows for a better conveyance of the light to the distal portion of the light distributor via a "mirror effect", of which the intrinsic light absorption must not exceed 10%. This local treatment is located on the proximal side on the second wall inside the sealed cavity of the light distributor, and can be carried out by soaking or by spraying a metal material.

According to another characteristic, said photo-bioreactor comprises at least one means for bubbling with a supply of CO2, arranged at least on a portion of the bottom of the chamber of the photo-bioreactor, in such a way as to allow for a permanent stirring of said aqueous liquid comprising said photosynthetic culture. The terms "means for bubbling" means any means known to those skilled in the art able to supply within said chamber gas, in particular in the form of bubbles.

BRIEF DESCRIPTION OF THE FIGURES

Other characteristics, details and advantages of the invention shall appear when reading the following description, in reference to the annexed figures, which show.

For increased clarity, identical or similar elements are marked with identical reference signs on all of the figures.

DETAILED DESCRIPTION OF AN EMBODIMENT

Figure 1:
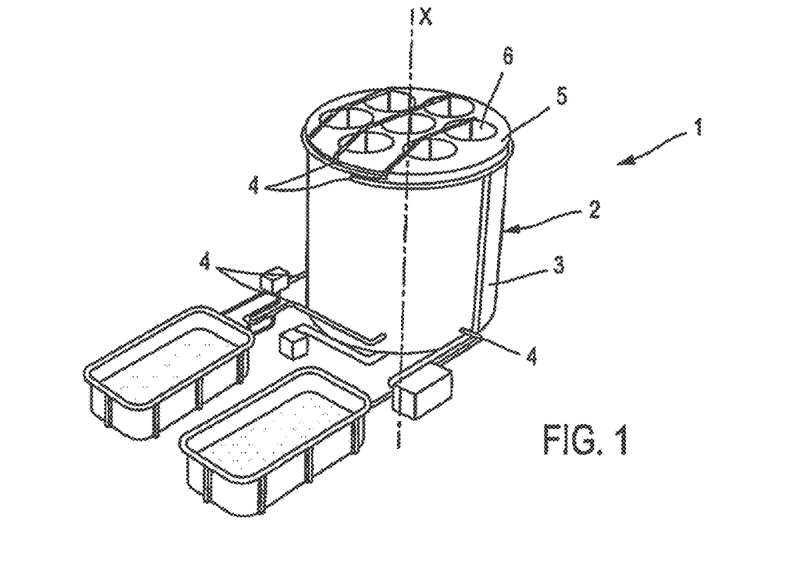
FIG. 1, discloses a 3D representation of an embodiment according to the invention, FIG. 2, discloses a 3D representation of an embodiment of the photo-bioreactor without the covering means.

FIG. 1 shows an embodiment of the invention wherein, the device for producing a photosynthetic culture 1 comprises at least one photo-bioreactor 2 forming a chamber 3 having a supply/discharge means 4, and able to contain an algal water. By way of example, the chamber can be a natural cavity such as a lake, a pond, or in the sea or artificial, made of concrete, steel, geo-membrane, etc. It can be painted white as such allowing for the reflection of the light, coated with a material that is waterproof, and/or thermally insulated from the inside and/or from the outside.

Said photo-bioreactor can have a cubic, parallelepiped, cylindrical, spherical, pyramid, prismatic shape of any variants of the latter. Preferably, a parallelepiped or cylindrical shape will be chosen of which the dimensions are suited for the industrial production of a photosynthetic culture. For example for a parallelepiped photo-bioreactor: 100 m by 30 m and 8 m high; or for a small cylindrical photo-bioreactor: 7 m in diameter over 4 m high. Of course, the dimensions of the photo-bioreactor will have to be determined and adapted according to the type of industrial installation desired.

Preferentially, said photo-bioreactor is above ground; or in order to limit the space occupied by such an installation, it can be buried partially. It can be placed in the vicinity of a factory that emits CO2, a waste water treatment plant, methanisers/digesters, in framework of recycling (Biogas, cogeneration, composting, recycling CO2). Moreover, it can be placed on arid land or in deserts, near the sea for the supply of water.

Said chamber 3 is covered on its proximal end, by a covering means 5, that is sufficiently resistant in order to at least tolerate the weight of a man once installed. For example a plastic tarp or a combination of layers of polymers, or a waterproof fabric of the polyester type with a PVC coating that is typically used for the covering of tents or tractor-trailer lorries.

The thickness of the covering means 5 is for example 0.6 mm with a weight of about 600 g/m2. Furthermore, the covering means 5 has at its periphery a means for attaching 21 in order to allow for a sealed/waterproof application on the walls of the chamber 3. This can be for example a seam with eyelets wherein tensioners pass, or sheaths wherein metal tubes are inserted. Furthermore, it can be advantageous for its density to be less than 1 so that it can float in order to facilitate its installation.

Figure 2:
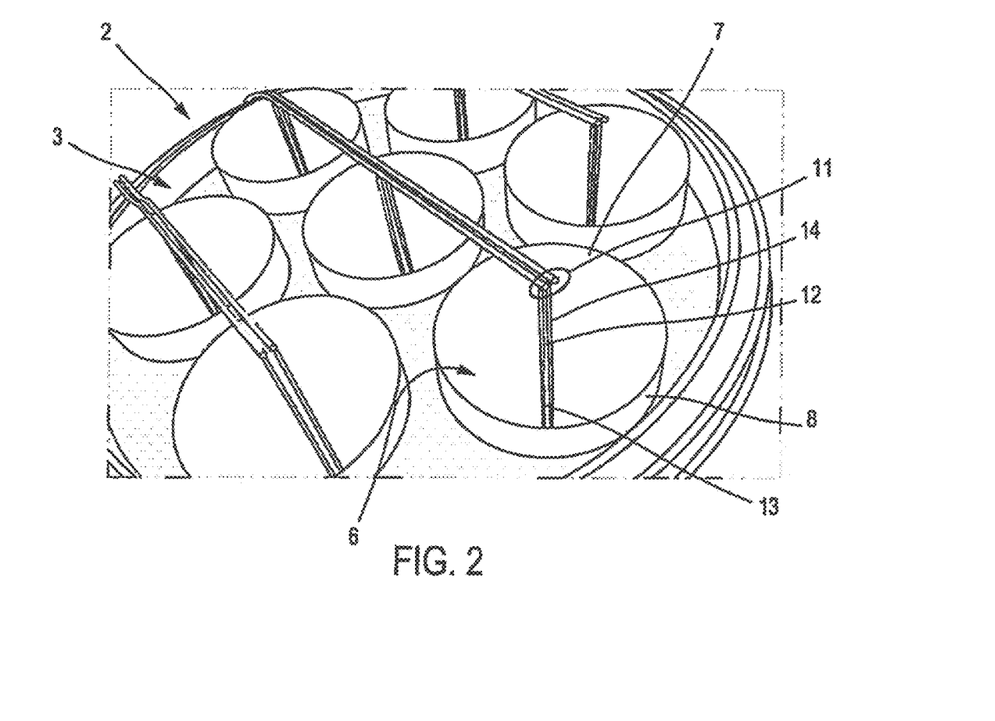

Said photo-bioreactor 2 is provided with at least one light distributor 6.

Said at least one light distributor 6 is more preferably of tubular, cylindrical shape, extending longitudinally according to an axis X, of which the dimensions are adapted to the dimensions of the photo-bioreactor.

The tubular shape of the light distributor 6 was retained because it is simple and easily carried out in the factory, even for large dimensions, in relation to other geometrical shapes.

Figure 4:
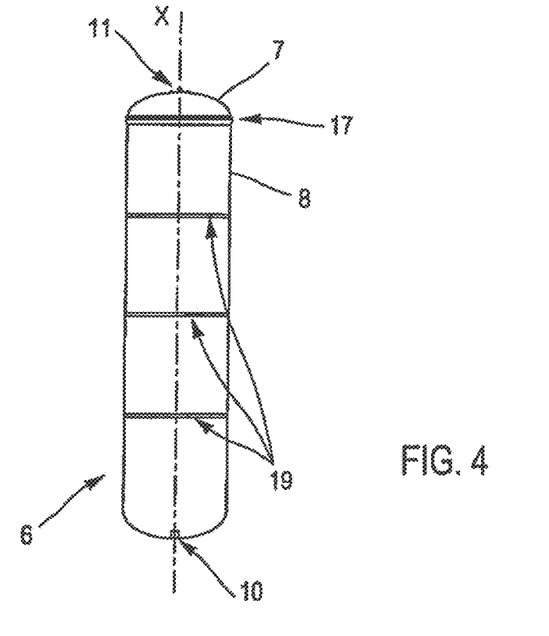
FIG. 4 is a longitudinal cross-section of an embodiment of a light distributor.

Said at least one light distributor or "tank" or "balloon" 6 is delimited by a flexible membrane more preferably made of polymer, able to vary the volume of said at least one light distributor 6 such as an inflatable/deflatable tank and has at least two walls, at least one first wall 7 arranged so as to receive the light at a proximal end, at least one second wall 8 arranged so as to emit at least one part of the received light.

The flexible membrane is more preferably slightly extensible and not elastic, in order to minimise the phenomenon of bloating on the tubular portion of the tank 6. The thickness of the membrane can be for example about 200 μm. The membrane allowing for the carrying out of the sealed cavity of the light distributor 6 can be comprised of several portions welded together. For example, a long tubular portion with two welded ends. The many transparent films used in particular for greenhouses, are very economical as they are manufactured in large quantities by blow film extrusion or co-extrusion. These manufacturing methods are very advantageous, because not only the costs of production are the lowest, but they make it possible to form multilayer films that combine different characteristics. Those skilled in the art will perfectly know how to use these known methods in order to manufacture the transparent film suited for the constitution of the walls 7 and 8 of the light distributor 6.

Furthermore, the degree of total luminous transmission of the membrane 7,8 is more preferably greater than 90%. The diffusing effect of the polymer must alter as low as possible its degree of luminous transmission. The transmission of light is an important property of the membrane. However, a distinction must be made between direct light and indirect light also called diffused light. Too much direct light can lead to a destruction of the micro-algae, and lost via absorption in caloric form, especially in regions with high solar radiation. Incorporating mineral fillers into the manufacture of the membrane makes it possible to obtain a better distribution of the light that becomes more diffuse and more homogenous. Furthermore, co-polymers (EVA type) have for function to block the radiation of long infrared, and slow down drops in temperature.

The light-receiving wall 7 in the proximal portion of the light distributor is preferably of a slightly domed shape. This shape allows for better capture of the light with respect to the position of the sun all throughout the day.

The dimensions, the number of light distributors 6 as well as the distance between each light distributor 6 are determined using the following formulas $$nb_{distributeur} = \frac{4 \cdot \xi \cdot S_{enceinte}}{\pi \cdot D^2} \quad (1)$$

$$H_{distributeur} = \frac{D}{4 \cdot q_2}(\eta \cdot q_{solaire} - q_2) \quad (2)$$

$$d = \sqrt{\frac{\pi \cdot D^2}{4 \cdot \xi \cdot \cos 30}} \quad (3)$$

distributeur=distributor
enceinte=chamber
solaire=solar

With:

Hdistributor: height of the second wall 8 of the light distributor 6 (immersed portion) (in m)

D: the diameter of the light distributor 6 (in m).

qsolar: incident flux of a sunny day (in μmoles of photons/m2·s−1)

q2: luminous flux desired at the light emitting wall of the light distributor for the good production of a given strain of micro-algae (in μmol/m2·s−1).

η: the transmission output between the first light-receiving wall 7 and the second emitting wall 8 of the light distributor.

nbdistributor: the number of light distributor 6 in the chamber 3 of the photobioreactor Schamber: surface of a chamber of rectangular or circular transversal section (in m2)

ξ: the volume fraction occupied by the light distributors, compared to the total volume of water in the chamber.

The fraction ξ is preferably between 0.6 to 0.8.

d: distance in meters between the longitudinal axes X of 2 light distributors.

Figure 5:
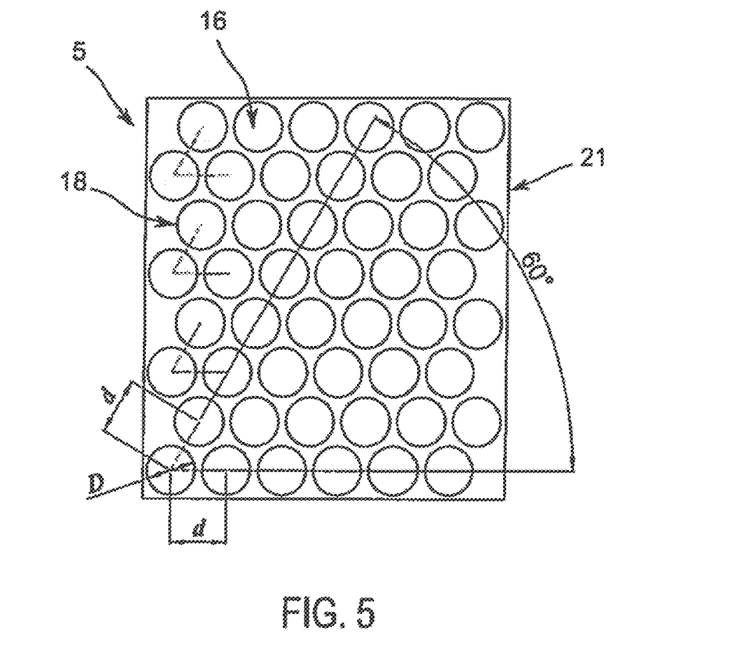
FIG. 5 is a top view of an embodiment of a portion of the covering means.

For the purposes of illustration, for a fraction epsilon ξ equal to 0.6857, and when the diameter D of each distributor is 2 meters, the distance d between the longitudinal axes X of 2 directly adjacent light distributors is 2.30 m, which is 30 cm of space between the walls such as shown in FIG. 5.

The distance d can be between for example 1m and 3 m.

The value epsilon ξ also represents in the proximal portion, the surface covered by all of said light distributors with respect to the total surface of the photo-bioreactor 2. A for example=0.667, ⅔ of the surface of the chamber 3 is covered by the first wall 7 of the light distributor 6, with the last third being covered by the covering means 5. For a fraction ξ between 0.6 and 0.8, the water contained in the light distributors therefore represents about 60% to 80% of the total volume of water in the chamber 3, and the algal water will represent 20% to 40% of the total volume of water.

Of course, the dimensions mentioned in this application of the photo-bioreactor 2 and of the at least one light distributor 6 are not complete and can change according to the performance obtained the ergonomics sought.

The number of light distributors can for example be between 1 and 10,000 per chamber 3. The light distributors 6 are arranged equidistantly from one another in the chamber 3 such as is shown in FIG. 5. This arrangement forms a succession of rows placed in staggered manner, i.e. one row is offset by half of the distance between two light distributors, with respect to the preceding row and the following one. This arrangement optimises the useful light surface in the volume of algal water.

The advantage of introducing light distributors into the algal water is primarily to manage the large quantity of excessive light flux of the sun. In a basin of the "raceway" type, during a sunny day, the quantity of light arrives directly on a horizontal body of water. If a part of the quantity of photons is absorbed by photosynthesis, a large part of the light energy will be lost in the form of heat. Indeed, micro-algae up to a specific threshold no longer absorb excessive luminosity, and inversely this can generate photo-inhibition. Furthermore, an excessive temperature of the water on the surface can inhibit the growth of the micro-algae and much water is lost through evaporation. A three-dimensional approach makes it possible to overcome these problems, by diffusing the luminous flux on a maximum surface area in such a way as to increase the quantity of photons captured by the micro-algae. Also, the penetration of the light to the distal portion of the tank 6 is crucial for good photosynthetic production, leading to the interest of a membrane with suitable characteristics that make it possible to capture the luminous flux of the sun as best as possible, and to diffuse it as homogeneously as possible over the entire surface of the second light-emitting wall 8.

The quantity of light qsolar varies according to the geographical latitude of the installation location of the production site. The illumination for a sunny summer day in France is 80,000 Lux, which is an incident flux qsolar of about 1,350 µmol/m2·s−1. The micro-algae only need a few µmoles of photons/m2·s−1 even a few dozen µmoles/m2·s−1 to exceed the point of compensation between respiration and photosynthesis, and as such begin to increase and multiply. The table hereinbelow includes the results of various studies published on the daily production of various micro-algae, according to the intensity of the luminous flux:

| Micro-algae strain | Cellular concentration in stationary phase (×10E6 cell/ml) | Biomass volume production (g/L/day) | Lipid production (g/L/day) | Luminous flux (µmol/m2/s) | References in literature |
|---|---|---|---|---|---|
| *Chlorella Vulgaris* | 6 | 0.037 | 40% | 76 | Illman et al. (2000) |
| *Chlorella Vulgaris* | | 0.485 | | | Dragone et al. (2011) |
| *Chlorella Vulgaris* | | 0.254 | | | Liang et al. (2009) |
| *Chlorella Vulgaris* | | 1.437 | | 400 | Shih-Hsin Ho et al. (2012) |
| *Chlorella Vulgaris* | | 0.39 | | 90 | Shih-Hsin Ho et al. (2012) |
| *Chlorella Vulgaris* | | 0.272 | 0.144 | | Yeh and Chang (2012) |
| *Chlorella Vulgaris* | 33.2 | | | 100 | Jean Hee Bae et al. (2011) |
| *Chlorella Vulgaris* | 64.9 | | | 100 | Jean Hee Bae et al. (2011) |
| *Chlorella Vulgaris* | 227.2 | | | | Zaleha & al. (2013) |
| *Nannochloropsis oculata* | 112.3 | | | 100 | Jean Hee Bae et al. (2011) |
| *Nannochloropsis oculata* | | 0.382 | 0.17 | | Su et al. (2011) |
| *Nannochloropsis oculata* | | | 0.151 | | Chiu et al. (2009) |
| *Nannochloropsis oculata* | (7.9 g/L) | 1.5 | | 21 | Ramanathan & al. (2011) |
| *Nannochloropsis sp.* | 22.5 | | | 34 | Roncallo & Al. (2012) |
| *Nannochloropsis sp.* | 37.5 | | | 34 | Roncallo & Al. (2012) |
| *Nannochloropsis sp.* | | 0.124 | 0.074 | | Jiang et al. (2011) |
| *Nannochloropsis sp.* | | | 0.148 | | Cheirsilp and Torpee (2012) |
| *Nannochloropsis sp.* | 107.3 | | | 100 | Jean Hee Bae et al. (2011) |
| *Nannochloropsis sp.* | 92.2 | | | 17 8 h/24 | Zaleha & al. (2013) |
| *Desmodesmus sp.* | | 0.762 | 0.263 | 700 | Shih-Hsin Ho et al. (2014) |
| *Desmodesmus sp.* | | 0.433 | 0.213 | 700 | Shih-Hsin Ho et al. (2014) |
| *Desmodesmus sp.* | | 0.67 | 0.302 | 700 | Shih-Hsin Ho et al. (2014) |

-continued

| Micro-algae strain | Cellular concentration in stationary phase (×10E6 cell/ml) | Biomass volume production (g/L/day) | Lipid production (g/L/day) | Luminous flux (μmol/m2/s) | References in literature |
|---|---|---|---|---|---|
| Scenedesmus obliquus | | 0.151 | | 60 | Shih-Hsin Ho et al. (2010) |
| Scenedesmus obliquus | | 0.201 | | 60 | Shih-Hsin Ho et al. (2010) |
| Nannochlorum sp. | 250 | | | 80 | Pereira et al. (2011) |
| Tetraselmis sp. | 40 | | | 80 | Pereira et al. (2011) |
| Tetraselmis sp. | (12.38 g/L) | | 0.173 | 30 12 h/24 | Mohd Shamzi & al. (2013) |
| Chaetoceros calcitrans | 20 | | | 52 | Robert & His (1987) |
| Chaetoceros calcitrans | 14.7 | | 35.40% | | Kwangdinata & al. (2014) |
| Chaetoceros calcitrans | (8.1 g/L) | 1.7 | | 21 | Ramanathan & al. (2011) |
| Chaetoceros calcitrans | 10 | | | 13 | Kaspar & al. (2013) |
| Chlamydomonas sp | 7.5 (4 g/L) | | 0.169 | 250 | Nakanishi & al. (2013) |
| Spirulina Platensis | (1.59 g/L) | | | 52 | Chauhan & Pathak (2010) |
| Spirulina Platensis | (1.84 g/L) | | | 77 12 h/24 | Gami & al. (2011) |

Although studies are very often carried out on small volumes in the laboratory, the disparity of production performances for a given illumination is substantial. Certain studies show however good volume production with a low illumination of a few dozen μmoles of photons/m2·s−1 only. One of the studies of Roncallo & al. (2012) gives a maximum concentration of micro-algae Nannochloropsis sp. of 37.5×106 cells/ml for a luminosity of about 34 μmol/m2·s−1 (2000 Lux) only, in a photo-bioreactor with a vertical column 25 cm in diameter. One of the studies of Ramanathan & al. (2011) shows a daily production of Chaetoceros Calcitrans up to 1.7 g/L·day−1, for a luminosity of only 21 μmol/m2·s−1 (1200 Lux), in vertical tubes 4.5 cm in diameter.

In current literature, the outputs in surface production in g/m2·day−1 are disparate. The results range from a few grams per m2·day−1 to 130 grams per m2·day−1. The Indian study of Sudhakar & al. (2012) shows for example surface outputs in a conventional basin of the raceway type of an average of 73 g/m2·day−1 and 76 g/m2·day−1 on two separate biomass production sites.

Taking the equation (2) with the values D and qsolar mentioned hereinabove as an example, starting with a quantity of light q2 emitted at the surface of the second wall 8 for example 85 μmol/m2·s that is sufficient for good growth of a given strain of micro-algae, and with a transmission output 11 at 80% in the sealed cavity of the tank 6, the height H of the second wall 8 of the light distributor is then 6 m.

| Luminous flux q2 emitted in the distributor with D = 2 m H = 6 m output = 80% | | | |
|---|---|---|---|
| | Cloudy sky | Good weather | |
| Lighting: | 25,000 | 80,000 | Lux |
| Incident flux q solar: | 430 | 1,377 | μmol/m2/s |
| q2 distributor: | 26 | 85 | μmol/m2/s |

The absorption of the visible radiation in the height of the water column of the light distributor 6 should be as low as possible in order to retain good output transmission η of the light. That is to say, have a filtered water with the lowest turbidity. In water, red light in the range of wavelengths between 600 to 700 μm is absorbed faster than blue light (400 to 500 μm). At a depth of 10 m, about 80% of the blue light is still available in a clear water, while the red will be entirely absorbed. However, all micro-algae photosynthesise blue light among others. Those skilled in the art will obviously take this into account, according to the desired height of water in the chamber 3. For example, with Diatoms, the production of lipids is favoured by blue wavelengths, precisely those which are the least quickly absorbed by the water. The water contained in the sealed cavity of the tank 6 can be fresh water or seawater. Most of the substances contained in sea salt have little effect on the absorption of the light in water. There is hardly any difference between the absorption spectrum of very clear seawater and that of distilled water.

A maximum quantity of photons of 300 μmol/m2·s−1 can be distributed over the surface of the second wall 8 of the tank 6. For a given quantity of PAR (Photosynthetically Active Radiation, expressed in μmol/m2·s−1 or in W/m2) at a geographical latitude, the average quantity of photons available in the chamber 3 obviously depends on the diameter of the light distributor proportionally to its depth, this quantity is calculated using the formula (2).

Furthermore, the maximum concentration of the micro-algae in the algal water is to be adapted for an optimum daily photosynthetic production. The semi-continuous production mode is interesting. It consists in concentrating the cellular density until the stationary phase, i.e. the threshold at which the micro-algae can no longer develop any further in a given culture medium and at a given luminosity. At this saturation threshold, a sampling of a portion of the algal water is carried out via the means for discharging 4, in order to be filtered and to recover the biomass therefrom. The study of Shih-Hsin Ho & al. (2014) shows that a sampling at 90% of the volume of algal water every 5 days allows for a better daily volume production of micro-algae *Desmodesmus* sp. than a sampling at 10% every two days (0.67 g/L/day compared to 0.20 g/L/day respectively). The frequency of the harvest will depend on the rapidity of the growth of the given strain of micro-algae, in order to reach the saturation threshold, and the quantity of algal water sampled at each harvest.

A production of bio-fuel can be calculated based on a theoretical volume productivity, with the figures in the following table:

| | | |
|---|---|---|
| Number of days of production: | 300 | days/year |
| Diameter D of the distributors 6: | 2 | m |
| Height H of the distributors 6: | 6 | m |
| Emitting surface of the distributors: | 40.86 | m2 |
| Fraction value Epsilon: | 0.7495 | |
| Distance d between distributors (at axes X): | 2.2 | m |
| Number of distributors/ha (equation 2): | 2,386 | |
| Number of surface m2 per hectare: | 97,490 | m2/ha |
| Volume of algal water: | 16,539 | m3/ha |
| Raceway depth equivalence: | 17 | cm |
| Surface production in distributor: | 60 | g/m2/j |
| Biomass volume production: | 0.354 | g/L/j |
| % of land unoccupied (paths, etc.): | 15% | par ha |
| Biomass production per hectare: | 1,492 | T/ha/year |
| % of lipids in the biomass: | 30% | |
| Annual production of Bio-carburant per ha: | 508,000 | L/ha/year |

In an alternative embodiment, the diameter of the first wall 7 can be different from the diameter of the second wall 8.

In another alternative embodiment of the invention, the first wall 7 receiving the light is made of a rigid plastic of the polycarbonate type, and the second wall 8 of the flexible membrane type. The interface between the two walls 7, 8 is sealed. Furthermore, the two walls can be separated for storage and/or maintenance.

Moreover, according to another embodiment, said tank 6 is provided at its proximal end with a ring for lifting or any other technically equivalent means able to extract said tank (more preferably in its deflated form), of said chamber 3.

Figure 3:
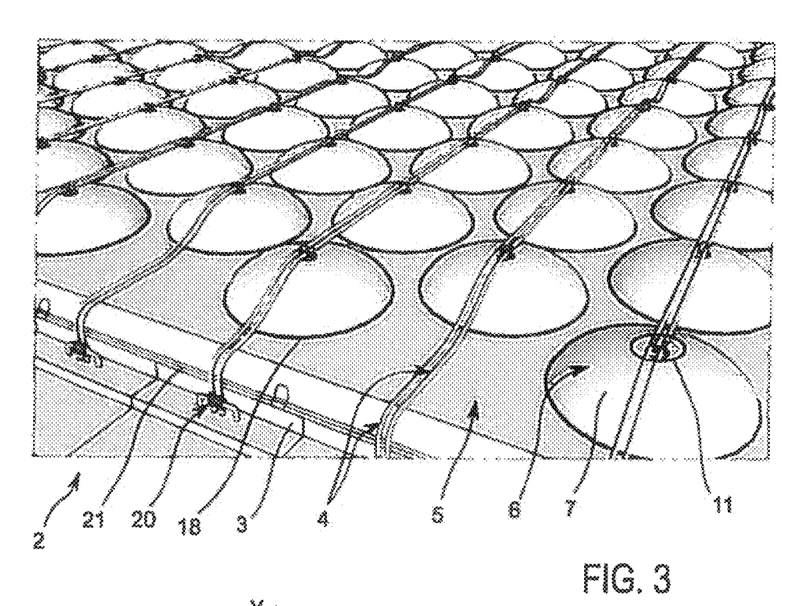
FIG. 3 is a detailed view of an embodiment of a light distributor installed in a photo-bioreactor according to the invention, maintained in a fixed position by the covering means.

Furthermore, said tank 6 is provided at its proximal end with independent means 11 for supplying and discharging, able to fill and to extract a fluid or fluids from the sealed cavity delimited by the walls 7 and 8, such as is shown in FIG. 3.

These means can be inserted welded to the wall 7 of the tank 6. These inserts comprise an internal tapping in order to allow for the connecting to circuits, and can be of different sizes according to the type of fluid to be circulated.

In a preferred embodiment, said fluids introduced into the sealed cavity are water and air, able to control the immersion of said at least one light distributor 6 in the algal water. The water contained in the sealed cavity is as clear as possible and filtered, for good luminous transmission on the surface as well as at depth.

In another embodiment, said at least one light distributor 6 has two sealed cavities separated by a transparent membrane, one for air in the proximal portion, one for water for the immersion in the distal portion.

Furthermore, so as to maintain immersed said at least one light distributor 6 along a plane parallel to the axis X, in the manner of a "fishing float", said at least one light distributor 6 is provided on its distal end with a mass 10. Said mass 10 can be made of metal, concrete, or a capsule made of moulded plastic filled with sand. The shape of the mass is preferably flat, so as to take up a minimum of space along the orthogonal axis X.

According to alternative embodiments, said mass 10 can: be screwed into an insert, hang along a line located at the distal end of said at least one tank 6, or more preferably be at the end of a guide 9 passing through said tank 6, or any other technically equivalent means.

Figure 6:
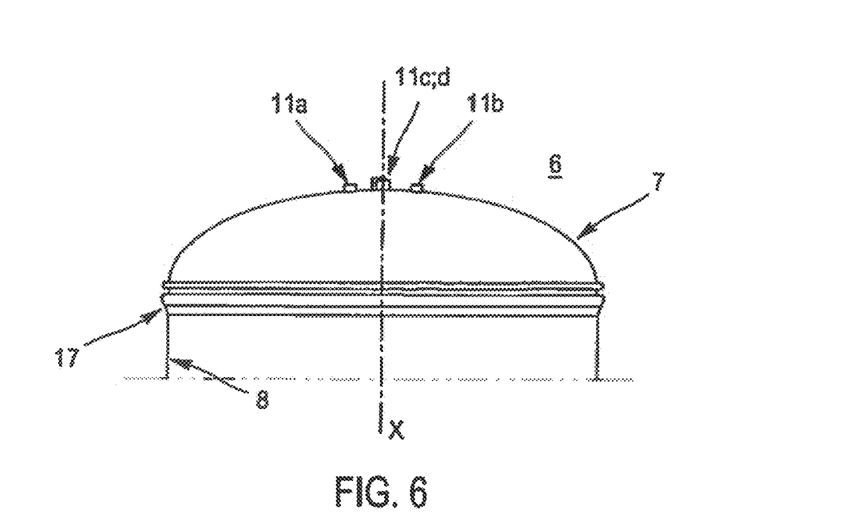
FIG. 6 is a diagram of the proximal end of an embodiment of said light distributor.
Figure 7:
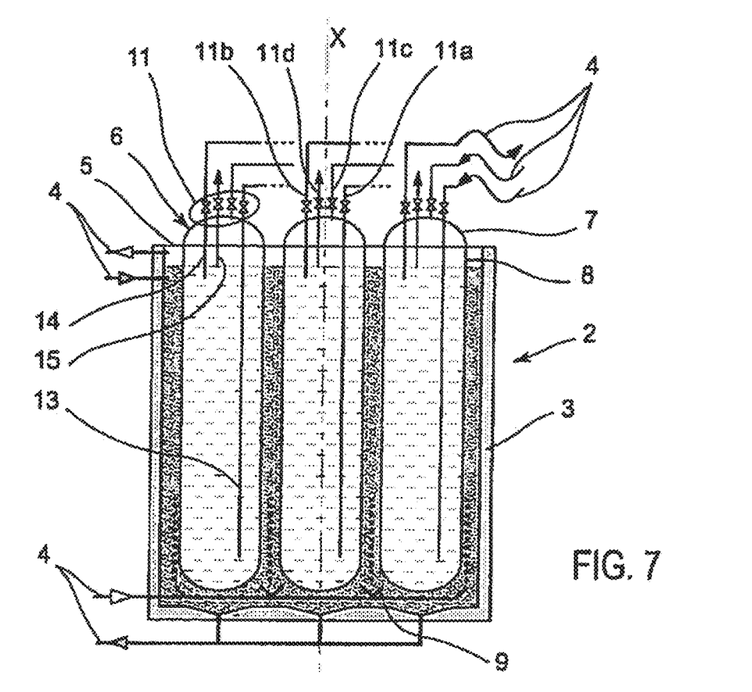
FIG. 7 is a diagrammatical cross-section orthogonal to the plane formed by the support of an embodiment of the network for supplying and extracting/discharging fluids from the photo-bioreactor, FIG. 8 discloses a representation in three dimensions of an embodiment on a large scale of a device for producing according to the invention comprising several photo-bioreactors.

In a preferred embodiment, said independent means 11 for supplying and discharging are comprised of a means for supplying with water 11a, of a means for discharging water 11b, of a means for supplying with air 11c and of a means for the escaping of air 11d, these means 11 can be comprised of valves, check valves or any other means known to those skilled in the art. FIGS. 6 and 7 show this arrangement. As such, such an arrangement can make it possible to isolate from the circuit for supplying and for discharging a specific distributor 6 during a maintenance phase without compromising the other light distributors 6 of said device for producing 1.

Furthermore as shown in FIGS. 2 and 7, the said means for supplying with water 11a is provided with a long pipe 13 that extends substantially along the longitudinal axis X and opens into the bottom of said tank; said means for discharging water 11b is provided with a short pipe 14 which opens below the plane formed by the interface between the water and the air, for example at 10 or 20 cm of said plane; said means for escaping/exhaust of air 11d is provided with an air discharging pipe 15 which opens on the plane forming the interface between the water and the air. This air discharging pipe 15 is able to establish the immersion depth of the tank 6 in the algal water by controlling the volume of air in the tank 6. Preferably, said short pipe 14, long pipe 13 and said air discharging pipe 15 are attached to said guide 12; furthermore, said means for supplying with air 11c, and said means for the escaping/exhausting of air 11d can be confounded such as shown in FIGS. 2, 4 and 6.

The means for supplying and discharging air 11c and 11d are simple physical means for absorbing the expansion or the contraction of the air inside the sealed cavity in the proximal portion of the light distributor 6, regardless of the fluctuation of the daily meteorological temperature. As such the volume of air in the proximal portion remains constant, providing good immersion of said tank 6 in the algal water.

Moreover, the log supply pipe 13 can also be used to empty the tank 6. In this case, it will be pierced preferably regularly over its entire length in order to empty said tank 6 better and as such prevent excessively quick clogging between the walls of said tank and the pipe 13. Another solution is that the pipe 13 is provided with a suction strainer at its end.

Optionally, the air discharge pipe can have different lengths in order to obtain a shift in height between for example two rows of tanks 6 in the photo-bioreactor 2. This can be particularly interesting in order to create a slight slope of the covering means 5, and as such facilitate the discharging of rainwater. As such the covering means can be for example further away from the distal portion at the middle of the photo-bioreactor than the sides. The drop can be slight, more preferably less than 2%.

Optionally, a level for measuring the height of the water contained in the sealed cavity of the light distributor 6 is connected to an external management electronic box (not shown). This level can be a fixed sensor or inserted on the guide 12 or on the long pipe 13.

The connections of said means 11 for supplying and for discharging on the means for discharging 4 interact with the means for managing via a ramp 10 that connected several light distributors 6, for example four tanks. Then at the edge of the chamber, the ramp is connected to the means for managing connecting for example a pumping room and filtration of the water and of the air of the tanks. For a large-size chamber, each row of tanks is for example supplied by several ramps connected end-to-end via flexible pipes together. Also in order to facilitate the maintenance in a localised manner, valves 20 are placed at the ends of the rows of tanks, and can be accessed from the edge of the chamber, in order to isolate the row in question from the rest of the circuit.

Optionally as shown in FIG. 4, said at least one light distributor 6 can be provided with at least one additional means 19 of maintaining that make it possible to rigidify its walls (maintain a tubular appearance of the light distributor 6) and to prevent a domed effect on the second wall. These means 19 can be strapping spaced over the height of the light distributor 6 or a localised excess thickness of the second wall.

As shown in FIG. 7, said photo-bioreactor comprises at least one means for bubbling 9 a gas more preferably air, in particular with an additional supply of CO2 (with possibly a supply of nutrients), arranged at least on one portion of the bottom of the chamber 3 of the photo-bioreactor 2, in such a way as to allow for a permanent stirring of said aqueous liquid comprising said photosynthetic culture and to discharge the oxygen produced by the photosynthesis outside of the algal water, as such making it possible to prevent the risk of a high over-saturation in oxygen and consequently an growth inhibition of the micro-algae. To do this, the ascension speed of the bubbles can preferably be between 0.3 to 0.35 m/s. Furthermore, preferably, said at least one means for bubbling 9 is not placed in line with said at least one light distributor 6; it is placed for example between two light distributors 6.

Moreover, the increase in the number of means for bubbling 9 at the m2 has for advantage to prevent the phenomena of "spiral-flows". This phenomenon of ascending current of the algal water created by the ascension of bubbles which accelerates the speed of passage of the latter, and affects the gaseous exchange. The rapprochement of the means of bubbling 9 between them breaks the risk of "spiral-flows".

The air diffused in the algal water can contain a concentration in CO2 that is more substantial than that of atmospheric air (400 ppm), with the purpose of decreasing the need in aeration and its cost. For example a proportion of the CO2 in the air supplied at 1000 ppm would be sufficient to divide by two approximately, the needs and costs in aeration, without affecting the proper discharging of the oxygen. The proximity of the device for producing 1 with a factory emitting CO2, or the supply with CO2 from the biomass digesters integrated into the device for producing would be a wise choice in order to optimise the costs of production.

The means for bubbling 9 can comprise membrane diffusers made of EPDM which allow for an aeration with fine bubbles. It has the form of discs fixed to the air supply network. The standard air diffusers used for the aeration of the basins of the treatment plants can be suitable as long as they are adapted to the pressure of the water column of said photo-bioreactor.

Furthermore, in an alternative embodiment, a mechanical means of stirring can be used in addition to said means for bubbling 9 for example with propellers.

Optionally, one or several LED lamps can be placed inside the sealed cavity of the light distributor 6, for example along the guide 12, and connected electrically. Such LED lamps make it possible to increase the daily photosynthetic production of the micro-algae. The LED lamps are preferably immersed in the water of the tank 6 for better luminous diffusion. They can have a power of several watts and preferentially emit in the wavelength range of the absorption of chlorophyll during photosynthesis (400 nm-700 nm). This illuminating can supplement the natural lighting on days of little sunshine, and/or operate at night, knowing that it can be interrupted according to the sequences in relation to the biological cycles of the micro-algae.

As shown in FIGS. 3 and 5, the covering means 5 of said proximal end of the chamber 3 of the photo-bioreactor 2 is provided with at least one opening 16 able to receive within and to maintain said at least one light distributor 6 in a stationary position in said chamber of the photo-bioreactor 2. As such when necessary, a light distributor 6 can be replaced without having to touch said covering means, or the other light distributors 6.

As shown in FIG. 6 showing an alternative embodiment, the maintaining of said at least one light distributor 6 in said at least one opening 16 is accomplished by cooperation of mechanical forms between a surface relief 17 of said at least one light distributor 6 and an edge 18 of said opening 16.

Said surface relief 17 can be a negative relief in the wall of said at least one light distributor 6 such as a groove or recess wherein said edge 18 is housed, or a series of positive reliefs such as a rail or a bulge surrounding said edge 18, such as is shown in FIG. 6.

In an alternative embodiment, said surface relief 17 can be an intermediate sheath welded between the walls 7 and 8. One or several flexible strips or semi-rigid profiles can be inserted into the sheath in order to form the bulge or a pre-stressed ring ready to be housed in said opening 16.

Furthermore, the surface relief 17 can be an inflatable sheath independently of the sealed cavity of the light distributor 6.

Interestingly, said fluids within said at least one tank 6 create an overpressure, deforming the walls of said at least one light distributor. This makes it possible to create a sealed cooperation between the wall of said at least one light distributor 6 and the edge 18 of the opening 16 of the covering means or tarp 5.

In another alternative embodiment, said at least one light distributor 6 has a diameter that is slightly greater than that of said at least one opening 16; as such when said at least one light distributor is inflated the latter is jammed by the opening 16 during said cooperation of form.

Under the tarp 5, the discharging of the water saturated air (or possibly with ethanol) and oxygen, is done through means for discharging 4 such as pipes placed along said chamber 3 without excessive pressure, in order to prevent leaks. These gases are possible conveyed to a premises in order to recover the water, calories and oxygen from them.

As such, the evaporated water can flow through a condenser making it possible to dramatically decrease the supply of water during the operation of the photo-bioreactor. Suitable equipment can condense more than 90% of the evaporated water, and as such recycle it in the algal water of the chamber 3. This arranging method can furthermore be associated with an air/air or air/water calorie exchanger, or a heat pump because the air exiting the chamber 3, hotter and saturated, can easily heat the water supplying the tanks 6, or the air loaded with CO2 distributed in the algal water.

According to an alternative embodiment, the means for discharging 4 can be connected directly on the tarp 5.

According to the invention, supply/discharge means 4 such as outlet vents for filtered algal water are located on the walls of the chamber 3 of the photo-bioreactor, in particular towards the proximal end under the plane of algal water in order to allow for a filling without turbulence of the chamber with respect to said at least one light distributor 6. Furthermore, the emptying/draining of the algal water can be done by a discharge network crisscrossing the bottom of said chamber 3, for example, under each light distributor 6. The algal water can also join a storage basin or a treatment and filtration, centrifugation and transformation of the biomass plant, via suitable collector.

All of the collectors of the supply and return for the algal water, the water and the air of the light distributors, and the air used for bubbling, can be placed along several photo-bioreactors, be fixed at a height along outside walls of the chamber 3, be buried, be inserted between two wall surfaces separating two photo-bioreactors, or be a part of the structured set separating two photo-bioreactors.

Furthermore, the chamber of the photo-bioreactor is provided with sensors (level, temperature, composition, pH, salinity, turbidity, O2, CO2, etc.), meters and automatic control devices integrated into a system for managing.

In a particular embodiment of the invention, the nutrients used for the development of the culture medium are injected into the algal water after filtration, i.e. on a circuit that returns to the chamber 3.

Figure 8:
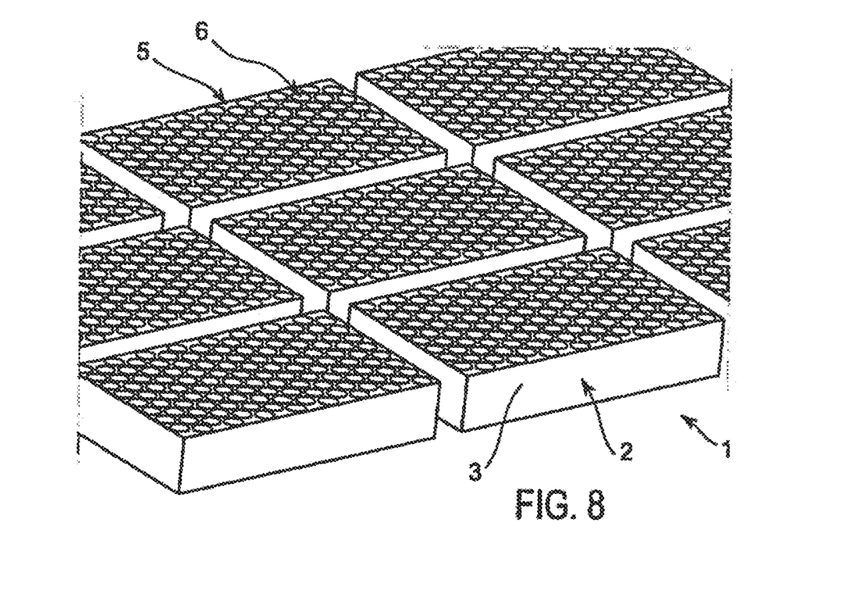

In order to obtain an installation of industrial size, said device for producing 1 can comprise a plurality of photo-bioreactors 2 of which the chambers 3 are installed side-by-side as shown in FIG. 8. In this case, the means for supplying, extracting and discharging as well as the means for controlling and managing and the means for storage, can be shared between the various photo-bioreactors or groups of photo-bioreactors.

Interestingly, the covering means 5 and the wall 7 of the light distributors 6 make it possible to obtain a greenhouse effect between the latter and the plane of algal water. The principle of the greenhouse is a simple means for capturing the excess solar energy that is not used by the photosynthesis of the micro-algae. Recovered in the form of heat, it contributes to the overall rise in the temperature of the culture medium.

The opportunity to use a photo-bioreactor of several meters in depth with a large volume of water has several advantages. First of all the stability of the temperature of the culture medium. Micro-algae are very sensitive to variations in temperature. The American study of James & Boriah (2010) shows that at a depth of 60 cm, the production of biomass is twice as substantial than at a depth of 10 cm, even with a lower luminosity, due to the better stability in temperature. The inertia generated by the volume of water is therefore very substantial in order to counter the oscillations in the daily atmospheric temperatures.

Furthermore, the volume of water contained in the chamber 3 makes it possible to dissipate the heat captured by this greenhouse effect in the proximal portion, as such preventing excess temperatures due to high amount of sunlight on the surface. The height of the water column is used somewhat as an accumulator of calories. As such, the light energy provided at the m2 by the sun is even further used by the photo-bioreactor, improving its output by extending the harvest season. Indeed this accumulation of heat is not lost and is used for the development of the micro-algae on bad weather days. The analogy can be made with that of vegetable growing in a greenhouse and a crop in an open field: the culture in a greenhouse allows for quasi-permanent production while it is only a few months in the open field. Another possible analogy, the temperature of the water of a swimming pool under a Plexiglas cover remains higher and for a longer period of time in the season compared to a swimming pool that is not covered.

So the depth of the chamber 3 will have to be adapted according to the geographical location of the photo-bioreactor, with the quantity of solar energy varying according to the latitude on Earth. For example a shallow basin on the equator will have a temperature of algal water that is too high for photosynthetic growth, because the dissipation of the heat will be too low.

On the other hand, the covering means 5 and the wall 7 of the light distributors 6 have an insulation function to inclement weather, via the layer of air that separates them from the plane of the water. As such the temperature of the culture medium in the proximal portion will be less influenced by the daily meteorological conditions (cool winds, warm winds, heavy rain, etc.).

The stirring of the algal water via the aeration of fines bubbles allows for the homogenisation of the temperature over the entire height of the water column. Also, the circulation of the water inside the sealed cavity of the light distributors 6 is substantial in order to homogenise the temperature from top to bottom in the chamber 3. The slow and continuous circulation of the surface water heated by the sun towards the distal portion of the light distributor is carried out by the independent means 11 for supplying and for discharging.

Furthermore, the temperature of the water of the sealed cavity can be regulated by adding or by removing exterior calories, for example a calorie exchanger or any other means of heating or cooling. As such, with such an inverted "water bath", the regulated temperature of each light distributor is dissipated and regulates in turn the temperature of the algal water in the chamber 3.

Implementing a Device According to the Invention

A method for implementation consists in sliding the tarp 5 above the chamber 3 full of water, by inserting the tanks 6 therein progressively from the edge of the chamber 3. The tarp 5 is taught and maintained at the surface of the water. Tanks 6 are placed in a first row of openings 16 of the tarp 5, and are connected together. Air is injected in order to allow them to float in the water of the chamber 3. And so on for the other rows, while having the tarp 5 advance in order to finally cover the chamber 3. The connection between the tarp 5 and the chamber 3 is made watertight. Water is added to the tanks 6 until pressurisation is obtained. Although the tightness already exists starting from this moment between said tank 6 and the opening 16, the edge 18 of the latter is not nested in the surface relief 17 of said tank 6. For this, air is injected under the tarp 5, while the air/water ratio in the tanks 6 decreases. The pressure under the tarp 5 raises the edge 18 of the opening 16 along the wall 7 of said tank 6 until its nesting in the relief 17.

According to another method of implementation, the tarp 5 can be installed above the chamber 3 filled beforehand with water, using a crane or mobile gantry. Said tanks 6 are placed through the openings 16 using a crane or a motorised gateway that is specially developed for this task. Said tanks 6 are deployed, connected, filled with water and with air with a low air/water ratio. The membrane of said tank 6 is then stretched by the pressurising. The air/water ratio in said tanks 6 is increased in such a way that they raise the tarp 5. As a whole, the tarp 5 is now suspended by said tanks 6. The nesting between the edge 18 of said opening 16 and the surface relief 17 of said tank 6 can take place thanks to a force exerted downwards on the tarp 5 using tools adapted for this purpose. The waterline of each tank 6 can be adjusted by blowing in air until it is discharged by a pipe 15 provided for this purpose. The level of the algal water and that of the tanks 6 can be adjusted in such a way as to obtain a tarp height 5 that is slightly higher at the edge of the wall of the chamber 3, in order to facilitate the flow of rainwater towards the periphery of the photo-bioreactor.

Many combinations of embodiments can be considered without leaving the scope of the invention; those skilled in the art will choose one or the other according to the economic, ergonomic, dimensional or other constraints that will have to be complied with.

The invention claimed is:

1. A device for producing (1) a photosynthetic culture comprising:
    at least one photo-bioreactor (2) forming a chamber (3) holding an aqueous liquid comprising a photosynthetic culture,
    a first fluid supply and discharge arrangement (4) connected to the chamber, the fluid supply and discharge arrangement operative to supply and discharge fluids from said chamber interacting with a management system,
    at least one light distributor (6) comprising:
      at least one first wall (7) arranged so as to receive the light at a proximal end,
      at least one second wall (8) arranged so as to emit at least one part of the received light,
      a sealed cavity defined by said at least one first wall (7) and said at least one second wall (8), with at least one part of the at least one second wall (8) being immersed in the aqueous liquid comprising the photosynthetic culture, and
      at least one fluid, at least partially filling said sealed cavity, and
    a cover (5) that covers said photo-bioreactor (2) and limits evaporation of said aqueous liquid,
    wherein said cover (5) has at least one opening (16), that keeps said at least one light distributor (6) in a stationary position in said chamber (3) of the photo-bioreactor (2), and
    wherein said at least one light distributor is a floating light distributor that supports the cover above an upper plane of algal water.

2. The device for producing a photosynthetic culture according to claim 1, wherein said at least one light distributor (6) is provided with a second fluid supply and discharge arrangement (11, 11a, 11b, 11c, 11d) independent from the first fluid supply and discharge arrangement (4) connected to the chamber, the second fluid supply and discharge arrangement operative to supply and extract fluid to and from said at least one light distributor (6).

3. The device for producing a photosynthetic culture according to claim 1, wherein said at least one light distributor (6) is provided with an anchor (10) arranged at a distal end.

4. The device for producing a photosynthetic culture according to claim 1, wherein said at least one light distributor makes it possible to support the cover above the plane of algal water at a distance between 10 and 50 cm.

5. The device for producing a photosynthetic culture according to claim 1, wherein the fluid, at least partially filling said sealed cavity, is comprised of water and of air, able to pressurise the interior volume of said at least one light distributor (6) in such a way as to render the cooperation of form watertight between the edge (18) of said opening (16) and said surface relief (17) of said at least one light distributor (6).

6. The device for producing a photosynthetic culture according to claim 1, wherein said photo-bioreactor (2) comprises at least one bubbler (9) with a supply of $CO_2$, arranged at least on a portion of the bottom of the chamber (3) of the photo-bioreactor (2), in such a way as to allow for a permanent stirring of the aqueous liquid comprising said photosynthetic culture.

7. The device for producing a photosynthetic culture according to claim 1, wherein said walls (7,8) of said at least one light distributor are formed by at least one flexible membrane made of polymer.

8. The device for producing a photosynthetic culture as claimed in claim 7, wherein said flexible membrane received or comprises at least one internal and/or external surface treatment from among the following: anti-drip, anti-dust, UV and/or infrared filter, UV stabilisers, diffusing effect, hydrophobic, anti-algae.

9. The device for producing a photosynthetic culture according to claim 1, wherein the number ($nb_{distributor}$) and the immersed height ($H_{distributor}$) of said at least one light distributor (6) and the spacing (d) between the different light distributors (6) are determined using the following formulas:

$$nb_{distributeur} = \frac{4 \cdot \xi \cdot S_{enceinte}}{\pi \cdot D^2} \quad (1)$$

distributeur=distributor
  $\xi$: the volume fraction occupied by the light distributors (6), compared to the total volume of water in the chamber (3),
  D: the diameter of the light distributor (6) (in m),
  $S_{chamber}$: the surface of a chamber (3) of circular or rectangular transversal section (in m²), $$H_{distributeur} = \frac{D}{4 \cdot q_2}(\eta \cdot q_{solaire} - q_2) \quad (2)$$

distributeur=distributor
solaire=solar
  $H_{distributor}$: height of the second wall (8) of the light distributor (immersed portion) (in m),
  $q_{solar}$: incident flux (in µmoles of photons/m²·s⁻¹),
  $q_2$: luminous flux desired at the light emitting wall of the light distributor for production of a given strain of micro-algae (in µmole/m²·s⁻¹), η: the transmission output between the first light receiving wall (7) and the second emitting wall (8) of the light distributor $$d = \sqrt{\frac{\pi \cdot D^2}{4 \cdot \xi \cdot \cos 30}} \quad (3)$$

d: distance between the longitudinal axes X of 2 light distributors (6) (in m).

10. The device for producing a photosynthetic culture according to claim 9, wherein said at least one light distributor (6) is provided with a second fluid supply and discharge arrangement (11, 11a, 11b, 11c, 11d) independent from the first fluid supply and discharge arrangement (4) connected to the chamber, the second fluid supply and discharge arrangement operative to supply and extract fluid to and from said at least one light distributor (6).

11. The device for producing a photosynthetic culture according to claim 1, wherein at least one edge (18) of said opening of said cover (5) together with a surface relief (17) of said at least one light distributor (6) provides an arrangement that maintains said at least one light distributor (6) in a stationary position in said chamber (3) of the photobioreactor (2).

12. The device for producing a photosynthetic culture according to claim 11, wherein the number ($nb_{distributor}$) and the immersed height ($H_{distributor}$) of said at least one light distributor (6) and the spacing (d) between the different light distributors (6) are determined using the following formulas:

$$nb_{distributeur} = \frac{4 \cdot \xi \cdot S_{enceinte}}{\pi \cdot D^2} \quad (1)$$

distributeur=distributor
- ξ: the volume fraction occupied by the light distributors (6), compared to the total volume of water in the chamber (3),
- D: the diameter of the light distributor (6) (in m),
- $S_{chamber}$: the surface of a chamber (3) of circular or rectangular transversal section (in m$^2$), $$H_{distributeur} = \frac{D}{4 \cdot q_2}(\eta \cdot q_{solaire} - q_2) \quad (2)$$

distributeur=distributor
solaire=solar
- $H_{distributor}$: height of the second wall (8) of the light distributor (immersed portion) (in m),
- $q_{solar}$: incident flux (in μmoles of photons/m$^2$·s$^{-1}$),
- $q_2$: luminous flux desired at the light emitting wall of the light distributor for production of a given strain of micro-algae (in μmole/m$^2$·s$^{-1}$),
- η: the transmission output between the first light receiving wall (7) and the second emitting wall (8) of the light distributor $$d = \sqrt{\frac{\pi \cdot D^2}{4 \cdot \xi \cdot \cos 30}} \quad (3)$$

d: distance between the longitudinal axes X of 2 light distributors (6) (in m).

13. The device for producing a photosynthetic culture according to claim 11, wherein said wall (7) for receiving light of said at least one light distributor is arranged outside of the volume defined by said chamber (3) of the photobioreactor (2).

14. The device for producing a photosynthetic culture according to claim 11, wherein said at least one light distributor (6) is provided with a second fluid supply and discharge arrangement (11, 11a, 11b, 11c, 11d) independent from the first fluid supply and discharge arrangement (4) connected to the chamber, the second fluid supply and discharge arrangement operative to supply and extract fluid to and from said at least one light distributor (6).

15. The device for producing a photosynthetic culture according to claim 11, wherein the fluid, at least partially filling said sealed cavity, is comprised of water and of air, able to pressurise the interior volume of said at least one light distributor (6) in such a way as to render the cooperation of form watertight between the edge (18) of said opening (16) and said surface relief (17) of said at least one light distributor (6).

16. The device for producing a photosynthetic culture according to claim 1, wherein said wall (7) for receiving light of said at least one light distributor is arranged outside of the volume defined by said chamber (3) of the photobioreactor (2).

17. The device for producing a photosynthetic culture according to claim 16, wherein the number ($nb_{distributor}$) and the immersed height ($H_{distributor}$) of said at least one light distributor (6) and the spacing (d) between the different light distributors (6) are determined using the following formulas:

$$nb_{distributeur} = \frac{4 \cdot \xi \cdot S_{enceinte}}{\pi \cdot D^2} \quad (1)$$

distributeur=distributor
- ξ: the volume fraction occupied by the light distributors (6), compared to the total volume of water in the chamber (3),
- D: the diameter of the light distributor (6) (in m),
- $S_{chamber}$: the surface of a chamber (3) of circular or rectangular transversal section (in m$^2$), $$H_{distributeur} = \frac{D}{4 \cdot q_2}(\eta \cdot q_{solaire} - q_2) \quad (2)$$

distributeur=distributor
solaire=solar
- $H_{distributor}$: height of the second wall (8) of the light distributor (immersed portion) (in m),
- qsolar incident flux (in μmoles of photons/m$^2$·s$^{-1}$),
- $q_2$: luminous flux desired at the light emitting wall of the light distributor for production of a given strain of micro-algae (in μmole/m$^2$·s$^{-1}$),
- η: the transmission output between the first light receiving wall (7) and the second emitting wall (8) of the light distributor $$d = \sqrt{\frac{\pi \cdot D^2}{4 \cdot \xi \cdot \cos 30}} \quad (3)$$

d: distance between the longitudinal axes X of 2 light distributors (6) (in m).

18. The device for producing a photosynthetic culture according to claim 16, wherein said at least one light distributor (6) is provided with a second fluid supply and discharge arrangement (11, 11a, 11b, 11c, 11d) independent from the first fluid supply and discharge arrangement (4) connected to the chamber, the second fluid supply and discharge arrangement operative to supply and extract fluid to and from said at least one light distributor (6).

19. The device for producing a photosynthetic culture according to claim 16, wherein the fluid, at least partially filling said sealed cavity, is comprised of water and of air, able to pressurise the interior volume of said at least one light distributor (6) in such a way as to render the cooperation of form watertight between the edge (18) of said opening (16) and said surface relief (17) of said at least one light distributor (6).

* * * * *